US010551604B2

(12) United States Patent
Wu et al.

(10) Patent No.: US 10,551,604 B2
(45) Date of Patent: Feb. 4, 2020

(54) SPATIAL LIGHT MODULATOR BASED HYPERSPECTRAL CONFOCAL MICROSCOPES AND METHODS OF USE

(71) Applicant: Verily Life Sciences LLC, Mountain View, CA (US)

(72) Inventors: Cheng-Hsun Wu, Mountain View, CA (US); Charles Santori, Palo Alto, CA (US); Supriyo Sinha, Menlo Park, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 15/607,455

(22) Filed: May 27, 2017

(65) Prior Publication Data
US 2017/0343784 A1 Nov. 30, 2017

Related U.S. Application Data

(60) Provisional application No. 62/342,256, filed on May 27, 2016.

(51) Int. Cl.
*G02B 21/00* (2006.01)
*G01N 21/64* (2006.01)
(Continued)

(52) U.S. Cl.
CPC ........ *G02B 21/0032* (2013.01); *G01J 3/2823* (2013.01); *G01J 3/4406* (2013.01);
(Continued)

(58) Field of Classification Search
CPC ............ G02B 21/0032; G02B 21/0036; G02B 21/004; G02B 21/0076; G02B 21/16;
(Continued)

(56) References Cited

U.S. PATENT DOCUMENTS 5,587,832 A 12/1996 Krause
5,591,981 A 1/1997 Heffelfinger et al.
(Continued)

FOREIGN PATENT DOCUMENTS

EP 0916981 A1 5/1999
EP 2720075 A1 4/2014
(Continued)

OTHER PUBLICATIONS

Holoeye Photonics AG "PLUTO Phase Only Spatial Light Modulators" specification sheet, 2015.*
(Continued)

*Primary Examiner* — George G King
(74) *Attorney, Agent, or Firm* — Kilpatrick Townsend & Stockton LLP

(57) ABSTRACT

Systems and methods for confocal imaging are described. In one implementation, a confocal imaging system may include a light source configured to emit excitation light having one or more wavelengths, a sample holder configured to hold a sample, a two-dimensional (2-D) imaging device, a first set of optical elements, and a second set of optical elements. The first set of optical elements may include a first spatial light modulator (SLM) and at least one lens. The first set of optical elements may together be configured to collimate the excitation light, apply a predetermined phase modulation pattern to the collimated excitation light, and illuminate the sample in an excitation pattern.

20 Claims, 3 Drawing Sheets

(51) Int. Cl.
*G01J 3/44* (2006.01)
*G01J 3/28* (2006.01)

(52) U.S. Cl.
CPC ..... *G01N 21/6458* (2013.01); *G02B 21/0036* (2013.01); *G02B 21/0076* (2013.01); *G01J 2003/2826* (2013.01)

(58) Field of Classification Search
CPC .......... G01J 3/0229; G01J 3/10; G01J 3/2823; G01J 3/433; G01J 3/4406; G01J 2003/2826; G01N 21/6458; G01N 2021/6419; G01N 2021/6471; G01N 2201/0675
USPC ....................................................... 359/386
See application file for complete search history.

(56) References Cited

U.S. PATENT DOCUMENTS

| | | | |
|---|---|---|---|
| 6,399,935 | B1 | 6/2002 | Jovin et al. |
| 6,483,641 | B1 | 11/2002 | MacAulay |
| 6,794,658 | B2 | 9/2004 | MacAulay et al. |
| 7,339,148 | B2 | 3/2008 | Kawano et al. |
| 7,460,248 | B2 | 12/2008 | Kurtz et al. |
| 7,532,323 | B2 | 5/2009 | Tang et al. |
| 8,629,413 | B2 | 1/2014 | Betzig et al. |
| 2004/0061914 | A1 | 4/2004 | Miyawaki et al. |
| 2006/0214106 | A1 | 9/2006 | Wolleschensky et al. |
| 2009/0309049 | A1 | 12/2009 | Van Dijk et al. |
| 2010/0314554 | A1 | 12/2010 | Galimberti et al. |
| 2011/0228267 | A1 | 9/2011 | Hayashi |
| 2012/0069344 | A1 | 3/2012 | Liu |
| 2012/0307247 | A1 | 12/2012 | Tan et al. |
| 2013/0100525 | A1 | 4/2013 | Chiang et al. |
| 2013/0181143 | A1* | 7/2013 | Betzig ................ G02B 21/0032 250/459.1 |
| 2013/0329270 | A1 | 12/2013 | Nielsen et al. |
| 2015/0085141 | A1* | 3/2015 | Dai ....................... G01J 3/2823 348/187 |
| 2015/0145981 | A1 | 5/2015 | Anhut et al. |
| 2015/0247796 | A1* | 9/2015 | Somekh ............... G01N 21/553 356/369 |
| 2015/0362713 | A1* | 12/2015 | Betzig ................ G02B 21/0064 250/459.1 |
| 2016/0202178 | A1 | 7/2016 | Acosta |
| 2016/0327779 | A1* | 11/2016 | Hillman .............. G02B 21/367 |
| 2017/0089837 | A1 | 3/2017 | Matsumoto et al. |
| 2017/0176338 | A1 | 6/2017 | Wu et al. |
| 2018/0177401 | A1* | 6/2018 | Yang ....................... H04N 7/18 |

FOREIGN PATENT DOCUMENTS

| | | |
|---|---|---|
| GB | 859208 A | 1/1961 |
| JP | S5214417 A | 2/1977 |
| JP | S63101818 A | 5/1988 |
| JP | 2015-219501 A | 12/2015 |
| WO | 2015157769 A1 | 10/2015 |
| WO | 2016115018 A1 | 7/2016 |

OTHER PUBLICATIONS

Qing Ye et al., "High-efficiency electrically tunable phase diffraction grating based on a transparent lead magnesium niobate-lead titanite electro-optic ceramic", Optics Letters, Optical Society of America, vol. 36, No. 13, Jul. 1, 2011, pp. 2453-2455.
Yanli Zhang et al., "High-efficiency, liquid-crystal-based, controllable diffraction grating", Journal of the Optical Society of America, vol. 22, No. 11, Nov. 2005, p. 2510.
Sirleto L. et al., "Electro-Optical Switch and Continuously Tunable Filter Based on a Bragg Grating in a Planar Waveguide With a Liquid Crystal Overlayer", Optical Engineering, Soc. of Photo-Optical Instrumentation Engineers, vol. 41, No. 11, Nov. 2002, pp. 2890-2898.
International Search Report of International Application No. PCT/US2016/067684 dated Mar. 9, 2017.
International Search Report of International Application No. PCT/US2017/027510 dated Jul. 7, 2017.
Cha et. al., "Nontranslational three-dimensional profilometry by chromatic confocal microscopy with dynamically configurable micromirror scanning", Applied Optics, vol. 39, No. 16, Jun. 1, 2000.
Hanley et al., "An optical sectioning programmable array microscope implemented with a digital micromirror device", Journal of Microscopy, vol. 196, Pt. 3, pp. 317-331, Dec. 1999.
Hagen et al., "Biological applications of an LCoS-Based Programmable Array Microscope (PAM)", Proc. of SPIE vol. 6441, 2007.
Chakrova et al., "Development of a DMD-based fluorescence microscope", Proc. of SPIE, vol. 9330, 2015.
De Beule et al., "Generation-3 programmable array microscope (PAM) with digital micro-mirror device (DMD)", Proc. of SPIE, vol. 7932, 2011.
Hanley et al., "Highly Multiplexed Optically Sectioned Spectroscopic Imaging in a Programmable Array Microscope", Applied Spectroscopy, vol. 55, No. 9, 2001.
Matsumoto et al., "High-quality generation of a multispot pattern using a spatial light modulator with adaptive feedback", Optics Letters, vol. 37, No. 15, Aug. 1, 2012.
Stockley et al., "Liquid crystal spatial light modulator for multispot beam steering", Society of Photo Instrumentation Engineers, 2004.
Martial et al., "Programmable Illumination and High-Speed, Multi-Wavelength, Confocal Microscopy Using a Digital Micromirror", PLOS One, vol. 7, Issue 8, Aug. 2012.
Krizek et al., "Spatial light modulators in fluorescence microscopy", Formatex 2010.
Matsumoto et al., "Stable and flexible multiple spot pattern generation using LCOS spatial light modulator", Optics Express, vol. 22, No. 20, Aug. 2014.
Heintzmann, "Structured Illumination Methods", Handbook of Biological Confocal Microscopy, Third Edition, 2006.
Xun et al., "System for demonstrating arbitrary multi-spot beam steering from spatial light modulators", Optics Express, vol. 12, No. 2, Jan. 26, 2004.
International Search Report of International Application No. PCT/US2017/034875 dated Aug. 21, 2017.
International Search Report of International Application No. PCT/US2017/034877 dated Aug. 17, 2017.
International Application No. PCT/US2017/034877, "International Preliminary Report on Patentability", Dec. 6, 2018, 11 pages.

* cited by examiner

SPATIAL LIGHT MODULATOR BASED HYPERSPECTRAL CONFOCAL MICROSCOPES AND METHODS OF USE

CROSS-REFERENCE TO RELATED APPLICATION

This application claims the benefit of and incorporates by reference the content of U.S. Provisional Pat. App. No. 62/342,256, filed May 27, 2016.

BACKGROUND

Technical Field

The present disclosure generally relates to the field of imaging and to microscopy systems and methods. More particularly, and without limitation, the disclosed embodiments relate to systems and methods for confocal imaging through the use of spatial light modulators.

Background Description

Fluorescence microscopy uses principles of fluorescence to highlight structures for examination instead of light absorption, phase or interference effects. It can be applied, for example, in biology and other disciplines for characterizing samples. In fluorescence microscopy, fluorophores or other optical labels in a sample are excited by an excitation light beam directed towards the sample. Upon excitation, the fluorophores emit fluorescent light that can be acquired as an image.

When imaging thick samples, optical techniques can be employed to perform optical sectioning, i.e., obtain images of high resolution in the axial direction. One such technique is confocal microscopy. The most common approaches for performing confocal microscopy is to use a spatial pinhole that rejects light emitted from planes that are outside of the focal plane. Because the out-of-focus fluorescent light is substantially reduced or eliminated, confocal microscopes achieve good axial resolution. Therefore, confocal microscopy can further allow for reconstructing a three-dimensional (3-D) image (e.g., a virtual volumetric image) of a sample from the images obtained at a series of focal planes along the axial direction.

In confocal microscopy, optical sectioning is achieved by using point illumination and detection. The excitation light source, usually a laser beam, is focused to a spot and scanned across the sample or the sample is translated in the transverse direction with the laser spot being fixed. The fluorescent light collected from the sample then passes through a single pinhole to produce an optical section of the sample. A two-dimensional (2-D) image is generated by translating the pinhole or sample laterally on a point-by-point basis. To generate a virtual volumetric image, the sample or an objective is translated axially to adjust to a focal plane and the pinhole (or the sample) is scanned transversally to build up an image in that plane. This significantly limits the speed of image acquisition.

The speed of image acquisition can be increased by using parallel scanning techniques, such as the Yokogawa scanning units that use a Nipkow disk with an array of pinholes. When the Nipkow disk spins at high-speed, laser light passes through the pinholes on the disk in parallel and simultaneously illuminates many discrete points on the sample. However, the excitation pathway of the Yokogawa scanning units suffers from very low efficiency. The Nipkow disk typically rejects the vast majority of the excitation light because the spacing between neighbouring pinholes need to be large to maintain a reasonable degree of optical sectioning or confocality. Additionally, the size and spacing of the pinholes are fixed, and may only be optimized for one particular numerical aperture of the objective. Changing the degree of optical sectioning may require physically removing and replacing the disk, which can be troublesome, expensive, or not even possible in most systems.

Therefore, there is a need for methods and systems for confocal imaging that allows for rapid image acquisition, efficient utilization of excitation light, and easy adjustment of the pinholes.

SUMMARY

The embodiments of the present disclosure include systems and methods that improve the throughput or temporality of confocal microscopy by capturing light from a plurality of locations at a focal plane in a sample simultaneously. Advantageously, the exemplary embodiments allow for efficient utilization of excitation light and easy adjustment of a degree of optical sectioning by using spatial light modulators (SLMs), such as a micromirror device (DMD) or a liquid crystal device (LCD).

According to an exemplary embodiment of the present disclosure, a confocal imaging system is described. The system may include a light source configured to emit excitation light having one or more wavelengths, a sample holder configured to hold a sample, a two-dimensional (2-D) imaging device, a first set of optical elements, and a second set of optical elements.

The first set of optical elements may include a first spatial light modulator (SLM) and at least one lens. The first set of optical elements may be configured to collimate the excitation light, apply a predetermined phase modulation pattern to the collimated excitation light, and illuminate the sample in an excitation pattern. The excitation pattern may be at a Fourier plane of the phase modulation pattern. The second set of optical elements may include a second SLM and at least one lens. The second set of optical elements may be configured to image emission light collected from a focal plane in the sample to the imaging device. The focal plane may be conjugate to a pinhole pattern formed by pixels of the second SLM.

According to a further exemplary embodiment of the present disclosure, a method for obtaining a confocal image is described. The method includes the steps of providing a light source that emits excitation light having one or more wavelengths, collimating the excitation light from the light source, applying, by a first spatial light modulator (SLM), a predetermined phase modulation pattern to the collimated excitation light, illuminating a sample in a two-dimensional excitation pattern, and imaging emission light collected from a focal plane in the sample to an imaging device. The excitation pattern may be at a Fourier plane of the phase modulation pattern. The focal plane may be conjugate to a pinhole pattern formed by pixels of a second SLM.

According to a yet further exemplary embodiment of the present disclosure, a method for configuring a confocal microscope to obtain a confocal image of a sample is described. The method includes the steps of providing a light source that emits excitation light having one or more wavelengths, collimating the excitation light from the light source, applying, by a first spatial light modulator (SLM), a predetermined phase modulation pattern to the collimated excitation light, illuminating a sample in a two-dimensional excitation pattern, and imaging emission light collected from a focal plane in the sample to an imaging device. The excitation pattern may be at a Fourier plane of the phase modulation pattern. The focal plane may be conjugate to a pinhole pattern formed by pixels of a second SLM.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Figure 1:
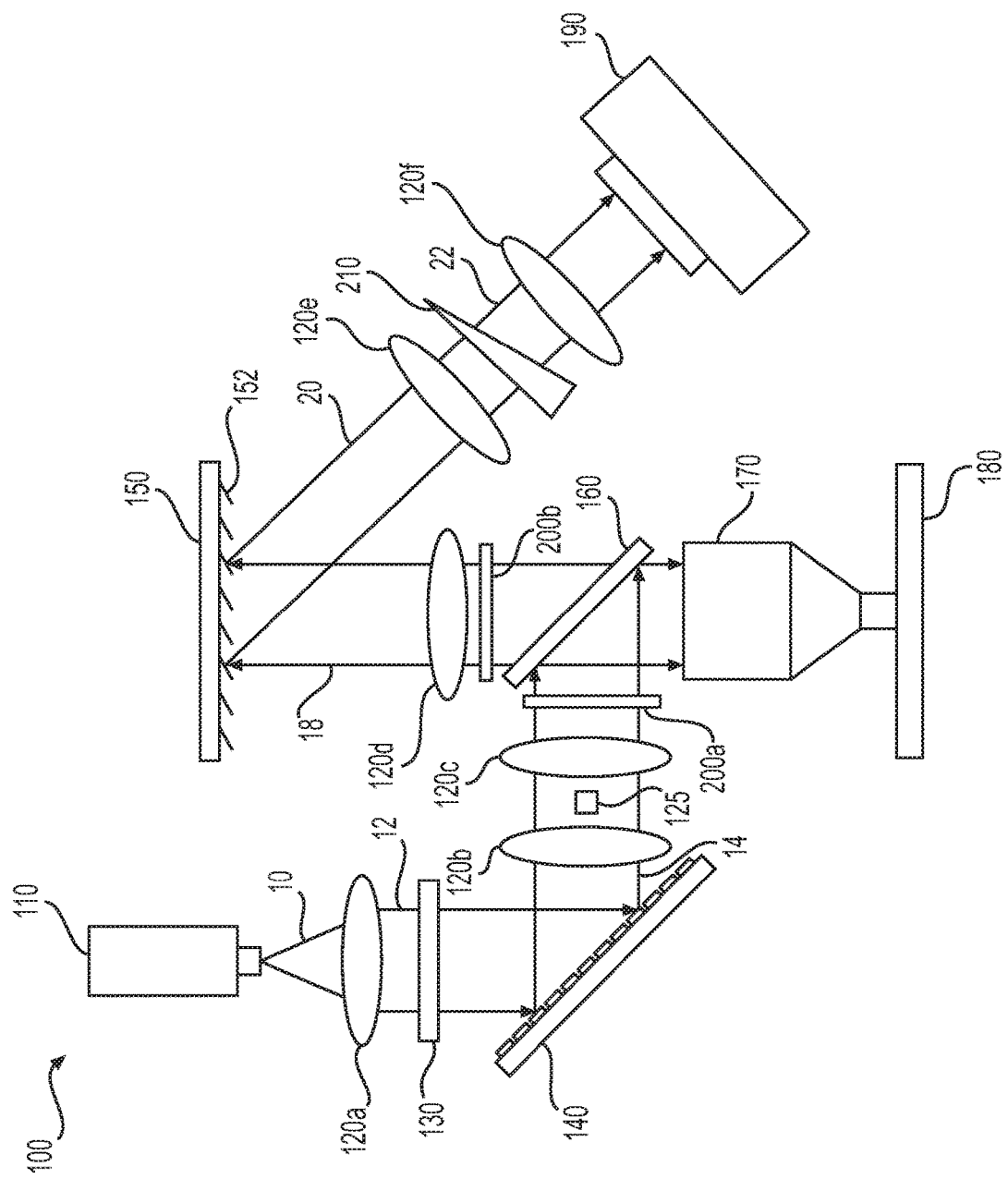
FIG. 1 is a schematic representation of an exemplary confocal imaging system, according to embodiments of the present disclosure.

The disclosed embodiments relate to systems and methods for achieving confocal imaging that allow for rapid image acquisition and efficient utilization of excitation light. Embodiments of the present disclosure may be implemented using a microscope, such as a fluorescence microscope, a confocal microscope, a transmission microscope, or a reflectance microscope, having one or more 2-D imaging devices, e.g., a CCD or CMOS sensor or camera. Alternatively, an optical imaging system may be built according to embodiments of the present disclosure using suitable optical elements.

Rather than using a Nipkow disk that has predetermined pinhole and/or microlens arrays, embodiments of the present disclosure allow for acquiring a 2-D image of a focal plane in a sample using programmable artificial pinholes with adjustable size and spacing. A plurality of 2-D images can be acquired at a plurality of focal planes and computationally reconstructed to obtain a 3-D or virtual volumetric image of a sample. Additionally, embodiments of the present disclosure allows for acquiring a hyperspectral confocal image dataset of a focal plane in the sample.

According to an aspect of the present disclosure, excitation light having one or more wavelengths may be used to excite fluorophores in the sample. The excitation light may be emitted by a single-color light source or a multi-color light source. In some embodiments, the single-color light source may be a pulsed or a continuous "single-wavelength" laser that emits light with a very narrow spectrum. In other embodiments, the single-color light source may be the output of a monochromator.

In some embodiments, the multi-color light source may have a continuous spectrum. For example, the multi-color light source may be a broadband light source, such as certain supercontinuum lasers, a white light source (e.g., a high-pressure mercury lamp, a xenon lamp, a halogen lamp, or a metal halide lamp), or one or more LEDs. In other embodiments, the multi-color light source may have a discrete spectrum. For example, the multi-color light source may be a combination of pulsed or continuous "single-wavelength" lasers that emit light with very narrow spectra.

According to an aspect of the present disclosure, excitation light emitted by the light source may be structured for illuminating a subset of areas on the sample in an excitation pattern using a first spatial light modulator (SLM). To structure the excitation light, the first SLM may modulate the phase or amplitude of the excitation light by selectively modulating, e.g., actuating or switching, its pixels. The pixels could either be digital or analog in modulation. The first SLM may be selected from a group of SLMs including a digital micromirror device (DMD), deformable mirrors (DM), a diffractive optical element, a liquid crystal device (LCD), and a liquid crystal-on-silicon (LCOS) device.

As described herein, an excitation pattern illuminated on a sample may include a plurality of focused spots of excitation light (excitation spots). The excitation pattern may be an arbitrary pattern or a predetermined pattern, such as a 2-D array of excitation spots simultaneously incident on the sample. Fluorophores or fluorescent molecules in the sample illuminated by the excitation pattern may be excited and subsequently emit fluorescent light.

In some embodiments, the excitation pattern may be scanned across the sample or the field of view by modulating the pixels of the first SLM. In other embodiments, an x-y translation stage may be used to scan the excitation pattern across the sample or the field of view by moving the sample or an objective in lateral directions. The stage may be a motorized translation stage, a piezoelectric translation stage, or any suitable stage that allows for lateral linear movement.

According to an aspect of the present disclosure, systems and methods according to the present disclosure allow for confocal optical sectioning. This allows for acquisition of images for a plurality of focal planes along an axial direction of the sample. In some embodiments, an image of a desired focal plane may be acquired by implementing one or more optical pinholes at a plane conjugate to the focal plane. The optical pinholes may be programmable artificial pinholes formed by pixels of a second SLM. The second SLM may be selected from a group of SLMs including a digital micromirror device (DMD), a liquid crystal device (LCD), and a liquid crystal-on-silicon (LCOS) device.

In some embodiments, a pinhole pattern may be formed by the pixels of the second SLM by selectively modulating or switching its pixels to match the excitation pattern of the excitation light. Advantageously, the pinhole pattern may allow for confocal imaging of a plurality of areas on the sample simultaneously illuminated by the excitation pattern. This may increase the speed and/or throughput of acquiring confocal images across the sample at the focal plane comparing to traditional confocal microscopes that use sequential point-by-point scanning. Additionally, a degree of optical sectioning or confocality may be advantageously adjustable as needed by changing the size and/or separation of the artificial pinholes formed by the second SLM, allowing for adjusting the degree of depth selectivity of the desired focal plane.

As described herein, fluorophores are used in this disclosure as an exemplary optical label in a sample. Descriptions in references to fluorophores are equally applicable to other types of optical labels consistent with the embodiments of this disclosure. For example, the excitation light emitted from the light source may also excite other types of optical labels, which upon excitation, may emit light with an emission spectrum. Therefore, fluorescent light and fluorescence emission spectrum used in the descriptions in this disclosure may also be used to represent the emission light and emission spectra of other optical labels.

According to an aspect of the present disclosure, systems and methods according to the present disclosure allows for hyperspectral imaging. Fluorescent light emitted by the fluorophores excited by the excitation light in a given area of the sample may be spectrally dispersed in a given lateral direction (e.g., the horizontal direction or the vertical direction). At least one dispersive element may be employed to spectrally disperse the fluorescent light into a fluorescence emission spectrum corresponding to that given area. The fluorescence emission spectra of a subset of areas on the sample may be acquired as a 2-D image in one exposure by the 2-D imaging device.

In some embodiments, fluorescence emission spectra of all the areas across the sample or across a field of view may be acquired by scanning the excitation pattern across the sample or the field of view. At each spatial location of the excitation pattern, a 2-D image of the fluorescence emission spectra corresponding to the excitation pattern may be acquired (e.g., each fluorescence emission spectrum corresponding to an excitation spot of the excitation pattern). Advantageously, a hyperspectral image dataset of the sample may be computationally reconstructed from a plurality of such 2-D images of the fluorescence emission spectra. Additionally, by forming a pinhole pattern that matches the excitation pattern using the second SLM during the scanning, a hyperspectral confocal image dataset of the sample can be obtained.

Reference will now be made in detail to embodiments and aspects of the present disclosure, examples of which are illustrated in the accompanying drawings. Where possible, the same reference numbers will be used throughout the drawings to refer to the same or like parts.

As described herein, to illustrate different wavelengths or frequencies of light, different densities of dotted texture are used in the attached drawings. Higher densities correspond to longer wavelengths or lower frequencies of light. Additionally, vertical and/or horizontal directions are used as examples for illustrating lateral or transversal directions.

FIG. 1 is a schematic representation of an exemplary confocal imaging system 100. In some embodiments, system 100 may be a fluorescence microscope, a transmission microscope, a reflectance microscope, or a confocal fluorescence microscope. Embodiments of the present disclosure are applicable to other suitable microscopy techniques for performing confocal imaging and/or hyperspectral imaging.

As shown in FIG. 1, system 100 may include an illumination system and a detection system. The illumination system may include a light source 110, a first SLM 140, and one or more lenses, e.g., lenses 120a, 120b, and 120c. The illumination system may further include a half-wave plate 130, an optical beam dump 125, and/or an optical filter 200a. The detection system may include a second SLM 150, a 2-D imaging device 190, and one or more lenses, e.g., lens 120d, 120e, and 120f. The detection system may further include a dispersive element 210 and/or an optical filter 200b. Depending on its layout, geometry, and/or application, system 100 may further include a beamsplitter 160, an objective 170, and a sample holder 180 where a sample to be imaged is placed. System 100 may include other optical elements, such as mirrors, beam dumps, an x-y translation stage, a z-axis translation stage or a tunable liquid lens (not shown), etc.

As described herein, an optical axis of system 100 may define a path along which the excitation light and emitted fluorescent light from the sample propagate through system 100.

In the illumination system, as shown in FIG. 1, light source 110 emits excitation light 10, which is directed to SLM 140. Excitation light 10 may be collimated and/or expanded using one or two lenses, e.g., lens 120a or a pair of lenses 120a. SLM 140 may structure collimated excitation light 12 through modulating the phase or amplitude of excitation light 12 by selectively actuating or switching its pixels. SLM 140 may be a transmission type or a reflection type SLM. While a reflection type SLM 140 is used in the exemplary embodiment shown in FIG. 1, a transmission type SLM 140 may alternatively be used consistent with the present disclosure. The geometry of the illumination system may be suitably designed based on the type of SLM 140.

As shown in FIG. 1, when SLM 140 is a reflection type SLM, at least a portion of the pixels of SLM 140 reflect excitation light 12 and direct the reflected excitation light 14 along the optical axis of system 100. In some embodiments, excitation light 14 may be directed by SLM 140 straight towards beamsplitter 160 and/or objective 170. In other embodiments, as shown in FIG. 1, reflected excitation light 14 may pass through one or more relay lenses, e.g., lenses 120b and 120c, before reaching beamsplitter 160 and/or objective 170. Objective 170 then focuses the excitation light to a sample placed on sample holder 180.

In the detection system, as shown in FIG. 1, fluorescent light 18 emitted by excited fluorophores in the sample is collected and/or collimated by objective 170. Fluorescent light 18 may pass through beamsplitter 160 and lens 120d along the optical axis of system 100. SLM 150 may be placed at about a plane conjugate to a focal plane located at a desired depth in the sample along the optical axis. For example, objective 170 and lens 120d may form an imaging configuration. When SLM 150 is a reflection type SLM, SLM 150 may reflect at least a portion of fluorescent light 18 and direct the reflected fluorescent light 20 along the optical axis of system 100 towards imaging device 190. Reflected fluorescent light 20 may pass a pair of tube lenses, e.g., lenses 120e and 120f, before reaching a 2-D sensor of imaging device 190.

As described herein, while a reflection type SLM 150 is used in the exemplary embodiment shown in FIG. 1, a transmission type SLMs 150 may alternatively be used consistent with the present disclosure. The geometry of the detection system may be suitably designed based on the type of SLM 150.

Functions and the working principles of various components of system 100 are described in detail below.

Light Source

As described above, light source 110 may be a single-color light source or multi-color light source. In some embodiments, excitation light 10 emitted by light source 110 may be linearly polarized. Additionally or alternatively, excitation light 10 may be collimated by lens 120a and become collimated excitation light 12 before being incident on SLM 140.

In some embodiments, collimated excitation light 12 may pass through half-wave plate 130. Half-wave plate 130 may change the polarization direction of a linearly polarized excitation light. For example, when SLM 140 is a LCD or LCOS device, half-wave plate 130 may rotate the polarization direction of the linearly polarized excitation light to be aligned in parallel with the orientation of the liquid crystal molecules in SLM 140. This may increase the efficiency of reflection and/or modulation of the excitation light by the pixels of SLM 140.

In some embodiments, light source 110 may be operably connected to a controller (not shown) having a processor and a computer-readable medium that stores instructions or operational steps. These instructions or steps, when executed by the processor, may modulate the operational states of light source 110. For example, the processor may activate or deactivate light source 110, modulate the duration of a pulse of a pulsed light source 110, and/or switch or tune the emission wavelengths of light source 110.

Spatial Light Modulator for Structuring Excitation Light

As described above, to structure excitation light 12 for illuminating the sample in an excitation pattern, SLM 140 may modulate the amplitude or phase of excitation light 12 by selectively modulating its pixels between operational states.

Amplitude Modulation

In some embodiments, the amplitude of excitation light 12 may be modulated by SLM 140. For example, SLM 140 may be a reflection type LCD or LCOS device. The LCD or LCOS device may be placed at a conjugate plane to the sample. In such instances, only one of lenses 120b and 120c may be placed between SLM 140 and objective 170. For example, lens 120b may be used as a tube lens and combined with objective 170 to form an imaging configuration. SLM 140 may be placed at about one focal length before lens 120b.

Pixels of SLM 140 may create an amplitude modulation pattern by manipulating the polarization of excitation light incident on the pixels. The amplitude modulation pattern may be imaged onto the sample as an excitation pattern by lens 120b and objective 170, for example. Depending on the focal lengths of lens 120b and objective 170, the excitation pattern may be a magnified or de-magnified image of the amplitude modulation pattern.

To create the amplitude modulation pattern, pixels of SLM 140 may be electrically modulated between an "on" state and an "off" state in a pixel-by-pixel fashion. The "on" pixels may rotate the polarization direction of linearly polarized light by about 90° while the "off" pixels do not perform the rotation. In such instances, a first linear polarizer (not shown) may be used to linearly polarize excitation light 12. A second linear polarizer or a polarizing beamsplitter (PBS) (not shown) may be used to pass excitation light 14 reflected by the "on" pixels and block excitation light 12 reflected by the "off" pixels.

A disadvantage of modulating the amplitude of excitation light 12 using SLM 140 is the loss of light during the modulation. This is because most of the pixels of SLM 140 are typically in the "off" state. Accordingly, most of excitation light 12 is steered away from the optical axis and would not reach the sample, and thus is lost.

Phase Modulation

To increase the efficiency of utilizing excitation light 12, SLM 140 may modulate the phase of excitation light 12 to generate the excitation pattern. In such instances, both lenses 120b and 120c may be placed between SLM 140 and objective 170. SLM 140 may be a reflection type LCD or LCOS device, for example. The LCD or LCOS device may be placed at an aperture plane, which may be a conjugate plane to the back aperture of objective 170 or a Fourier plane to the sample. For example, lenses 120b and 120c may form an imaging configuration. Lens 120b may be located about one focal length behind SLM 140. Lens 120c may be located about two focal lengths behind lens 120b. Objective 170 may be located about one focal length behind lens 120c.

The pixels of SLM 140 may form a custom phase modulation pattern to modulate the wavefront of excitation light 12. Upon the reflection of excitation light 12 by SLM 140, phases at different locations of the wavefront of the reflected excitation light 14 may be selectively changed according to the phase modulation pattern. In some embodiments, pixels of SLM 140 may be electrically modulated between an "on" state and an "off" state in a pixel-by-pixel fashion. If pixels of SLM 140 are in the "on" state, they may change the phase of the reflected light by changing the optical path length of light traveled in the liquid crystal; and if they are in the "off" state, they may not change the phase of the reflected light. This allows the phase modulation pattern formed by the pixels of SLM 140 to be digitally customized as needed. In other embodiments, pixels of SLM 140 may have multiple states or levels of phase adjustment (e.g., 256 levels between 0 and $2\pi$) and may be individually modulated to desired states or levels. Advantageously, increasing the states or levels of adjustment of the pixels increases the continuity of the adjustment of the phase modulation pattern and thus the adjustment of the phase of excitation light 14, and may further reduce undesirable diffraction orders in the excitation pattern.

The phase modulation may render wavelets of reflected excitation light 14 having different directions and/or phases. As reflected excitation light 14 propagates along the optical axis, each of the lenses 120b and 120c and objective 170 may perform Fourier Transform on the wavefront of reflected excitation light 14. A diffraction pattern may then be formed at the focal plane of objective 170. This diffraction pattern is referred to herein as the excitation pattern when illuminated on the sample.

In some embodiments, optical beam dump 125 may be placed along the optical axis between lenses 120b and 120c, e.g., about a focal length behind lens 120b or at a conjugate plane of the sample. This may allow the lower-order diffraction spots, e.g., zero-order and/or first-order diffraction spots, of a diffraction pattern formed by reflected excitation light 14 at the location of optical beam dump 125 to be substantially absorbed and blocked from reaching the sample. Because the excitation pattern is an image of the diffraction pattern formed at the location of optical beam dump 125, the intensity of lower-order diffraction spots of the excitation pattern illuminated on the sample would be substantially reduced. Since the lower-order diffraction spots, e.g., zero-order and/or first-order diffraction spots, are typically brighter than other orders of diffraction spots, the use of optical beam dump 125 may advantageously improve the uniformity of the intensity of the excitation pattern across the field of view.

As described above, the phase modulation pattern is at or approximately at a Fourier plane to the sample. In such instances, the electrical field of reflected excitation light 14, whose phase has been modulated by the phase modulation pattern of SLM 140, is further subject to Fourier Transforms by the lenses 120b and 120c and objective 170 before it illuminates the sample in a desired excitation pattern. In some embodiments, the excitation pattern may be an intensity profile of the wavefront of the transformed excitation light with a desired phase profile. The desired phase profile may be predetermined to increase the diffraction efficiency of the excitation light.

In some embodiments, computer algorithms, e.g., the Gerchberg-Saxton (GS) algorithm, may be used to generate the phase modulation pattern that would result in a desired excitation pattern. Further, customized computer algorithms may be used to generate time-varying phase modulation patterns for scanning or translating the desired excitation pattern across the field of view.

Advantageously, modulating the phase of excitation light 12 would allow it to propagate with substantially uniform intensity in the near field of SLM 140 and thus reduce loss of excitation light 12. The modulated excitation light may then form a customizable or programmable excitation pattern when illuminated on the sample in the far field. Therefore, comparing to modulating the amplitude of excitation light 12 as described above, modulating the phase of excitation light 12 to create a desired excitation pattern may substantially increase the efficiency of illumination of system 100 by reducing loss of excitation light 12.

SLM 140 may alternatively be a transmission type device implemented along the optical axis. The geometry of the illumination system may be suitably designed such that the amplitude or phase modulation pattern formed by the pixels of the device may modulate the amplitude or phase of excitation light 12 similarly as described above.

Whether SLM 140 modulate the amplitude or phase of excitation light 12, the excitation pattern illuminated on the sample can be programmed and customized as needed by modulating pixels of SLM 140 between two operational states in a pixel-by-pixel fashion. Further, the excitation pattern may be translated or shifted across the sample or a field of view in a given spatial direction, such as the horizontal or vertical direction, by scanning or changing the modulation of the pixels of SLM 140. For example, when SLM 140 is located at a Fourier plane of the sample for modulating the phase of excitation light 12, the excitation pattern may be scanned by changing the slope of a linear phase ramp along a spatial direction. This advantageously allows for scanning the excitation pattern across the field of view of system 100 without moving the sample and/or sample holder 180 using an x-y translation stage.

In some embodiments, depending on the type and modulation features of the pixels of SLM 140, excitation light 12 may be directed towards SLM 140 at a predetermined angle relative to a plane of SLM 140. The predetermined angle may depend on the type of SLM 140 and/or the geometry of system 100. For example, when SLM 140 is a reflection type SLM, excitation light 12 may be directed towards SLM 140 at an angle such that reflected excitation light 14 propagates along the optical axis of system 100.

In some embodiments, SLM 140 may be operably connected to a controller (not shown) having a processor and a computer-readable medium that stores instructions or operational steps. These instructions or steps, when executed by the processor, may modulate the operational states of the pixels of SLM 140 to form a desired excitation pattern and/or to translate the excitation pattern in a desired spatial direction over a predetermined distance across the field of view.

Multiple Illumination Sources

In some embodiments, the system 100 could be configured to illuminate a sample in the sample holder 180 with light at multiple different wavelengths simultaneously and/or sequentially. This could include operating multiple different light-emitting elements of the light source 110 to emit light at respective different wavelengths. Additionally or alternatively, multiple different light sources, SLMs, relay lenses, or other elements could be provided to facilitate illumination of the sample at multiple different wavelengths.

In some examples, this could include applying illumination from multiple different light sources to the first SLM 140. An angle of incidence of excitation light from each of the light sources onto the first SLM 140 could be selected such that, for a pattern of operation of the first SLM 140 that applies a phase grating pattern of phase shifts to incident/transmitted light at a given spatial period, the first SLM 140 diffracts the incident light at the two different wavelengths from respective different angles in substantially the same direction (e.g., a direction that propagates, via the objective 170 and/or other elements of the system 100, to the sample holder 180).

In some examples, the system could include an additional light source, an additional SLM, and/or additional other optical elements (e.g., additional lenses, pairs of relay lenses, optical dumps, half-wave plates, or optical filters) to provide an appropriately phase-shifted, focused, or otherwise specified excitation light to the sample holder 180 via the objective 170. This could include combining such additional excitation light to the excitation light 10 emitted by the light source 110 and modified by the first SLM 140 using, e.g., a beam splitter, a dichroic mirror, or some other optical elements.

Confocal Optical Sectioning

As described above, system 100 allows for confocal optical sectioning, which allows for selecting the depth of a focal plane in the sample. The depth of the focal plane may be selected by introducing one or more optical pinholes at a plane conjugate to the selected focal plane.

SLM 150 is used for achieving confocal optical sectioning. As described above, SLM 150 may be placed at about a plane conjugate to a focal plane located at a desired depth in the sample along the optical axis. Lens 120d may be used as a tube lens and together with objective 170 may form an imaging configuration. For example, as shown in FIG. 1, lens 120d may be located behind objective 170 and SLM 150 may be located about one focal length behind lens 120d. The space between the back aperture of objective 170 and lens 120d is a collimated space, which may be adjusted as need based on various factors, such as the geometry of system 100 and a desired location of a minimum beam aperture. In some embodiments, lens 120d is placed about one focal length behind objective 170.

In some embodiments, SLM 150 may be a digital micromirror device (DMD) having an array of multiple micromirrors 152. These micromirrors may be individually actuated to switch between two operational positions, an "on" position and an "off" position. When a micromirror is configured to be in the "on" position, fluorescent light 18 from the focal plane in the sample is reflected to propagate along the optical axis as reflected fluorescent light 20, which is directed to imaging device 190. When a micromirror is configured to be in the "off" position, fluorescent light 18 is reflected towards a direction deviated from the optical axis and is not directed to imaging device 190. In some embodiments, fluorescent light 18 reflected by the "off" micromirrors may be directed to other optical elements, such as a mirror or a beam dump (not shown).

In some embodiments, the micromirrors are of a square shape having a length of its sides ranging from about a few micrometers to about 10 μm. Other shapes and sizes of the micromirrors are also possible and may be suitably used. The DMD is typically capable of changing or alternating the "on" and "off" positions of the micromirrors very rapidly.

In some embodiments, a single micromirror of the DMD may be referred to as a single pixel. In other embodiments, a plurality of micromirrors may be referred to as a single pixel. For example, a group of immediately adjacent micromirrors may be referred as a single pixel and may be modulated or actuated in unison.

Pixels of SLM 150 may be selectively actuated or switched to "on" or "off" positions to form a pinhole pattern matching (conjugating) the excitation pattern illuminated on the sample. The pinhole pattern may include a plurality of artificial optical pinholes at the conjugate plane and reject out-of-focus fluorescent light from the sample. Therefore, out-of-focus fluorescent light would not pass through the detection system and are substantially removed or eliminated from the acquired image by imaging device 190.

The size and separations of the artificial pinholes in the pinhole pattern are programmable, and may be customized based on the excitation pattern and the magnification of the imaging configuration formed by objective 170 and lens 120d. For example, an artificial pinhole in the pinhole pattern may be formed by an array of "on" pixels to match the size of an excitation spot in the excitation pattern.

The fluorescent light 20 reflected by the "on" pixels of SLM 150 may then be imaged to imaging device 190 by lenses 120e and 120f. For example, lens 120e may be located about one focal length beyond the image produced by lens 120d (e.g., about one focal length behind SLM 150) such that it re-collimates reflected fluorescent light 20. Imaging device 190 may be located about one focal length behind lens 120f or at a conjugate plane of SLM 150. Because the fluorescent light is collimated in the space between lenses 120e and 120f, the distance between lenses 120e and 120f may be adjusted as desired. In some embodiments, lens 120f may be about two focal lengths behind lens 120e such that a plane midway between lenses 120e and 120f is conjugate to an exit pupil of system 100.

By digitally changing and/or laterally shifting the excitation pattern using SLM 140 and the matching pinhole pattern correspondingly using SLM 150, the whole field of view may be scanned for acquiring a confocal image. By further scanning the field of view across the sample, the whole sample can be scanned to obtain a complete confocal image dataset of the sample.

In some embodiments, imaging device 190 may be suitably tilted to reduce aberrations and thus improve the quality of the acquired images. This is at least because the "on" pixels of SLM 150 may direct reflected fluorescent light 20 at an angle that is not perpendicular to the surface plane of SLM 150 such that an image plane formed by lenses 120e and 120f may be tilted. Aberrations caused by this tilting effect may be compensated by properly tilting imaging device 190.

To change or select a depth of the focal plane, in some embodiments, sample holder 180 may be installed on the z-axis translation stage. The desired depth of the focal plane may be selected by moving sample holder 180 along the optical axis using the z-axis translation stage. Alternatively, objective 170 may be installed on the z-axis translation stage and the desired depth of the focal plane may be selected by moving objective 170 along the optical axis. As describe herein, the z-axis translation stage may also include x-y translation capability to move the field of view of system 100 across the sample in lateral directions.

In some embodiments, when SLM 140 is at a Fourier plane for modulating the phase of excitation light 12, the focal depth may be adjusted by changing the phase modulation pattern formed by the pixels of SLM 140. In such instances, excitation light 14 modulated by the pixels of SLM 140 may, upon reflection, include a superposition of slightly diverging or converging beams determined by the phase modulation pattern. Depending on their degree of divergence or convergence, these beams would focus at increased or reduced depth after passing through the microscope objective.

In other embodiments, the desired depth of the focal plane may be selected by tuning the focus of a tunable liquid lens (not shown) placed behind objective 170. As described herein, the z-translation stage, the tunable liquid lens, and/or the phase modulation pattern of SLM 140 may be controlled by a computer program to achieve autofocusing.

Advantageously, a degree of confocality may be adjusted as needed by changing the size and/or separation of the artificial pinholes formed by SLM 150. For example, increasing the sizes of the pinholes by increasing the number of pixels in the pinholes and/or reducing the pinhole spacing may reduce the degree of confocality and thus the degree of depth selectivity of the desired focal plane. On the other hand, decreasing the size of the pinholes by reducing the number of pixels in the pinholes and/or increasing the pinhole spacing may increase the degree of confocality and thus the degree of depth selectivity of the desired focal plane. In some embodiments, the depth selectivity may be proportional to the ratio of the number of "off" and "on" pixels of SLM 150. Therefore, SLM 150 may advantageously allow for switching between wide-field imaging and confocal imaging as desired by conveniently adjusting the pinhole size and/or separation.

Additionally, the pinhole pattern formed by pixels of SLM 150 advantageously allows for confocal imaging of a plurality of areas on the sample simultaneously illuminated by the excitation pattern generated by SLM 140. This may increase the speed and/or throughput of acquiring a confocal image dataset across the sample at the desired focal plane comparing to traditional confocal microscopes that use sequential point-by-point scanning.

Hyperspectral Imaging Capability

In some embodiments, hyperspectral imaging capability may be advantageously added to system 100 to allow for acquiring a hyperspectral-imaging dataset at a selected focal plane in the sample. A hyperspectral-imaging dataset may be represented in three-dimensions (3-D): two spatial directions (horizontal direction and vertical direction) and one spectral dimension (A). Information in the spectral dimension of a hyperspectral-imaging dataset may reflect fluorescence intensities as a function of a range of emission wavelengths of the fluorophores in the sample.

Hyperspectral imaging capability may be achieved by using dispersive element 210 in system 100. For example, dispersive element 210 may be located in the collimated space between lenses 120e and 120f. Dispersive element 210 may be a diffraction grating or a prism, such as a non-deviating prism (e.g., Amici prisms or double Amici prisms). Dispersive element 210 may spectrally disperse fluorescent light 20 reflected from SLM 150 along a given lateral direction. Spectrally dispersed fluorescent light 22 then passes through lens 120f and is acquired by imaging device 190.

Figure 2:
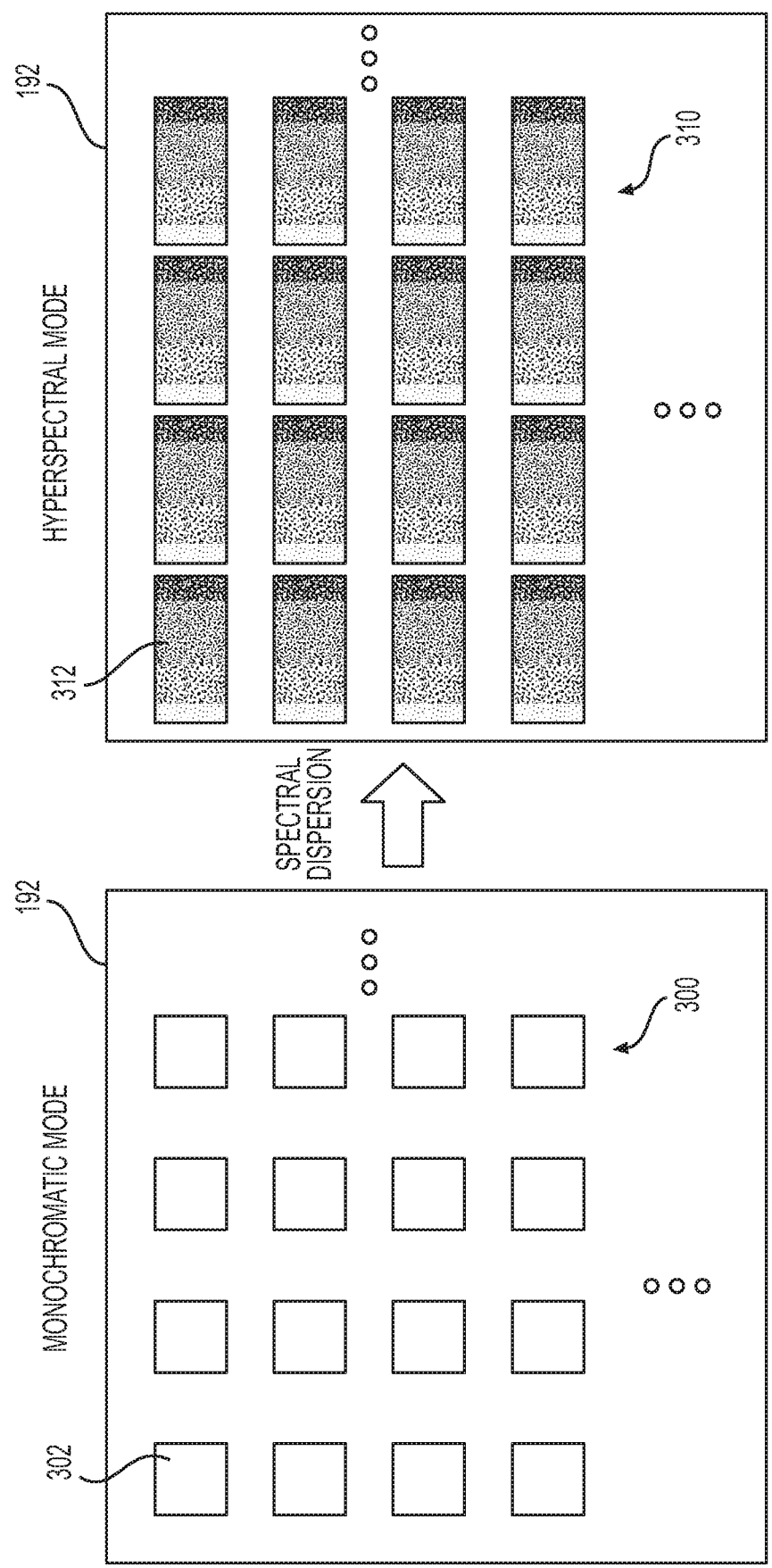
FIG. 2 is a graphical illustration for an exemplary scheme for performing hyperspectral confocal imaging, according to embodiments of the present disclosure.

FIG. 2 is a graphical illustration for an exemplary scheme for performing hyperspectral confocal imaging, according to embodiments of the present disclosure. In some embodiments, when system 100 is in a monochromatic imaging mode, imaging device 190 may acquire an image of fluorescent light 20 reflected by a pinhole pattern formed on SLM 150. The pinhole pattern conjugates an excitation pattern illuminated on the sample. For example, a 2-D image 192 acquired by imaging device 190 may show a 2-D array 300 of fluorescent spots 302 corresponding to a 2-D array of excitation spots in the excitation pattern.

In other embodiments, when system 100 is in a hyperspectral imaging mode, fluorescent light 20 reflected by SLM 150 is spectrally dispersed by dispersive element 210 in a given direction, e.g., the horizontal direction. In such instances, 2-D image 192 acquired by imaging device 190 may show a 2-D array 310 of fluorescence emission spectra 312. Each fluorescence emission spectrum 312 may be dispersed in the horizontal direction and correspond to an excitation spot of the excitation pattern at a different spatial location on the sample.

As described above, the excitation pattern may be laterally shifted, e.g., in the vertical and horizontal directions to scan across the field of view or the sample. At each spatial position of the excitation pattern, array 310 of fluorescence emission spectra 312 corresponding to the areas on the sample illuminated by the excitation pattern can be acquired in a 2-D image 192. A plurality of 2-D images 192 of fluorescence emission spectra may be acquired corresponding to a series of excitation patterns laterally shifted from one another and then computationally reconstructed to obtain a hyperspectral-imaging dataset.

Therefore, by digitally changing and/or laterally shifting the excitation pattern and the matching pinhole pattern on SLM 150 correspondingly, the whole field of view may be scanned for acquiring a hyperspectral-imaging dataset of a sample at a focal plane. By further scanning the field of view across the sample, the whole sample can be scanned to obtain a complete hyperspectral-imaging dataset of the sample at the focal plane.

The spatial separation, horizontal and/or vertical, between excitation spots of an excitation pattern may be predetermined based on various factors, such as the excitation wavelengths, the size of the sample, the field of view of system 100, the desired measurement throughput, spatial resolution, and/or speed, and the amounts of spectral dispersion of fluorescent light 22. For example, the spatial separation between the excitation spots in the horizontal direction may be predetermined based on the range of fluorescence emission spectra 312 in the horizontal direction such that the fluorescence emission spectra 312 do not overlap with each other in the horizontal direction in 2-D image 192.

The degree of spectral dispersion caused by dispersive element 210 may be predetermined based on various factors, such as the spectral range of fluorescent light 20, the size of the sample or the field of view, the size of imaging device 190, the desired spectral resolution, and the application of system 100.

In some embodiments, the degree of spectral dispersion caused by dispersive element 210 may be advantageously adjustable. For example, dispersive element 210 may be a pair of double Amici prisms placed along the optical axis of system 100. At least one of the pair of double Amici prisms is rotatable relative to the other around the optical axis. The rotation of the double Amici prisms relative to each other may allow for continuous control of the amount and/or angular orientation (e.g., dispersion angles) of the spectral dispersion of fluorescent light 22.

Lenses and Objective

Various lenses of system 100, such as lenses 120a-120f, may be achromatic, such as achromatic doublets or triplets, to limit or reduce the effects of chromatic and/or spherical aberration of the system. Further, objective 170 of system 100 may be achromatic. Alternatively or additionally, objective 170 may be an infinity-corrected objective such that objective 170 may form a desired focus (e.g., focused spots or focused pattern) of a collimated light beam entering from its back aperture. Using achromatic lenses and/or achromatic or infinity-corrected objective may allow fluorescent light of different wavelengths from a focal plane in the sample to similarly form a focused image at imaging device 190. Therefore, using achromatic lenses and/or achromatic objective may improve the quality of confocal images acquired by system 100.

Optical Filters and Beamsplitter

In some embodiments, optical filter 200a may be added in the illumination system along the optical axis. Optical filter 200a may be a clean-up filter that substantially transmits desired wavelengths of excitation light 12 and blocks unwanted wavelengths. For example, optical filter 200a may have a narrow passband ranging for about a few nanometers to block noisy spontaneous emission from light source 110 or to substantially reduce background noise.

Because the intensity of excitation light 12 may be orders of magnitude stronger than fluorescent light 18, excitation light 12 reflected and/or scattered by the sample and/or sample holder 180 may enter the detection system and affect the detection or acquisition of the fluorescent light by imaging device 190. Therefore, embodiments of the present disclosure may reduce or block excitation light 12 from propagating into the detection system as described below.

In some embodiments, beamsplitter 160 may be used to block excitation light 12 from propagating towards imaging device 190. Beamsplitter 160 may be a long-pass dichroic beamsplitter that substantially reflects the wavelengths of excitation light 12 and transmits at least a portion of the wavelengths of fluorescent light 18. The spectrum of excitation light 12 typically ranges from the ultraviolet through the visible spectra, and the spectrum of fluorescent light 18 typically ranges from the visible into the near infrared spectra. Therefore, the long-pass dichroic beamsplitter may block wavelengths of excitation light 12 and transmit a range of wavelengths of fluorescent light 18.

Alternatively or additionally, optical filter 200b may be added in the detection system along the optical axis. Optical filter 200b may be a notch filter that may substantially reflect the wavelengths or a narrow spectral band of excitation light 12, thereby blocking excitation light 12 from reaching imaging device 190.

In other embodiments, when excitation light 12 is linearly polarized, beamsplitter 160 may be a polarizing beamsplitter (PBS). The PBS may be selected such that it reflects light having a polarization direction same as that of the linearly polarized excitation light and to transmit light having a polarization direction perpendicular to that of the polarized excitation light. Most of the excitation light collected by objective 170 would therefore reflect from this PBS and would not reach imaging device 190. In some instances, both the sample and objective 170 may depolarize reflected or scattered excitation light to a small degree, and thus undesirably allow some excitation light to transmit through the PBS and enter the detection system.

Imaging Device

Imaging device 190 may include a suitable 2-D sensor located at an image plane conjugate to a selected focal plane in the sample. The sensor could be implemented with a CMOS sensor, a CCD sensor, a 2-D array of silicon avalanche photodiodes (APDs), or other suitable types of 2-D sensors.

Imaging device 190 may be operatively connected to a controller or a computing device (not shown) that controls its operation. For example, the controller (not shown) may have a processor and one or more computer-readable media that stores instructions or operational steps. The instructions or operational steps, when executed by the processor, may operate the exposure of imaging device 190, acquire 2-D images 192, and/or store the datasets of 2-D image 192 to a memory. The computer-readable medium may further store instructions or operational steps that, when executed by the processor, may perform data processing of the acquired 2-D image datasets and/or reconstruct a confocal image and/or a hyperspectral-imaging dataset from the 2-D image datasets.

Figure 3:
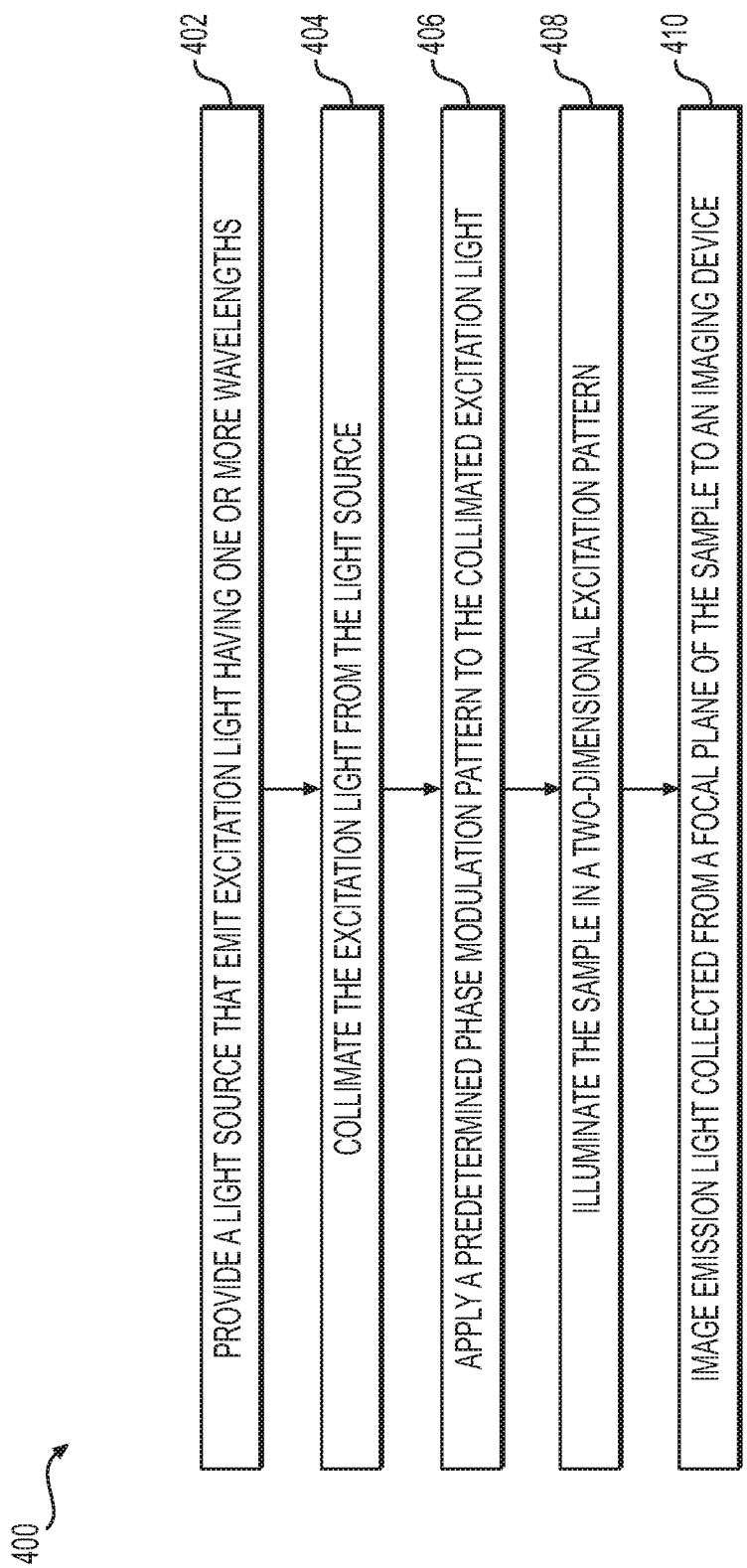
FIG. 3 is a flowchart of an exemplary method for obtaining a confocal image, according to embodiments of the present disclosure.

System 100 as described herein may be utilized in a variety of methods for confocal and/or hyperspectral imaging. FIG. 3 is a flowchart of an exemplary method 400 for performing confocal imaging or for acquiring a confocal image of a sample. Method 400 uses system 100 and features of the embodiments of system 100 described above in reference to FIGS. 1 and 2.

At step 402, light source 110 is provided and configured to emit excitation light 10 having one or more wavelengths. At step 404, excitation light 10 is collimated by lens 120a and become collimated excitation light 12. At step 406, collimated excitation light 12 is structured or modulated by being applied with a predetermined phase modulation pattern formed by pixels of SLM 140. At step 408, the structured excitation light is directed towards the sample and illuminates the sample in a two-dimensional excitation pattern. The excitation pattern is located at a Fourier plane of the phase modulation pattern. At step 410, emission light collected from a focal plane in the sample is imaged to imaging device 190. The focal plane can be conjugate to or at a conjugate plane of a pinhole pattern formed by the pixels of SLM 150.

Method 400 may further include additional steps. For example, method 400 may include calibrating system 100 before acquiring 2-D image 192. Various optical components in system 100 may be suitably calibrated and aligned such that focused 2-D images 192 with reduced or minimum aberration and/or distortion can be acquired.

Method 400 may further include spectrally dispersing fluorescent light 18 collected from the sample in a lateral direction using dispersive element 210. Spectrally dispersed fluorescent light 22 may be acquired in a 2-D image 192 by imaging device 190.

Method 400 may further include illuminating the sample sequentially in a series of excitation patterns laterally shifted from one another and forming a series of pinhole patterns matching the series of excitation patterns.

In some embodiments, method 400 may further include obtaining a plurality of 2-D images 192 of the emission light 20 corresponding to the series of excitation patterns, and reconstructing the plurality of 2-D images 192 to provide a confocal image. As described above, a 2-D image 192 may be acquired after each lateral shift of excitation pattern and the formation of its matching pinhole pattern. Each 2-D image 192 may record an array 300 of fluorescent spots 302 corresponding to each laterally shifted excitation pattern.

In other embodiments, method 400 may further include obtaining a plurality of 2-D images 192 of the spectrally dispersed emission light 22 corresponding to the series of excitation patterns, and reconstructing the plurality of 2-D images 192 to provide a hyperspectral confocal image dataset. As described above, a 2-D image 192 of the spectrally dispersed emission light may be acquired after each lateral shift of excitation pattern and the formation of its matching pinhole pattern. Each 2-D image 192 may record an array 310 of fluorescent emission spectra 312 corresponding to each laterally shifted excitation pattern.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

Instructions or operational steps stored by a computer-readable medium may be in the form of computer programs, program modules, or codes. As described herein, computer programs, program modules, and code based on the written description of this specification, such as those used by the controller, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A confocal imaging system, comprising:
 a light source configured to emit excitation light having one or more wavelengths;

a sample holder configured to hold a sample;
a two-dimensional imaging device; and
an optical system comprising:
a first spatial light modulator (SLM);
a second SLM;
a dispersive element, wherein the dispersive element is a pair of double Amici prisms; and
an objective; wherein:
the optical system is configured to (i) collimate the excitation light; (ii) apply, using the first SLM, a predetermined phase modulation pattern to the collimated excitation light; (iii) use the phase-modulated collimated excitation light to form an excitation pattern to illuminate the sample, wherein the excitation pattern is formed at a focal plane of the objective within the sample; (iv) collect emission light from the focal plane within the sample; (v) direct the collected emission light to the imaging device via the second SLM, wherein the focal plane within the sample is conjugate to a plane of a pattern of pinholes formed by pixels of the second SLM; (vi) use the dispersive element to spectrally disperse the collected emission light before the collected emission light reaches the imaging device; (vii) obtain, using the imaging device, a plurality of images of the spectrally dispersed emission light; and (viii) reconstruct the plurality of images to provide a hyperspectral confocal image dataset of the sample.

2. The system of claim 1, wherein the objective focuses the excitation light that has interacted with the first SLM onto the focal plane within the sample and collimates the emission light collected from the focal plane within the sample.

3. The system of claim 2, wherein the optical system further comprises one or more relay lenses, wherein the one or more relay lenses image the phase modulation pattern onto a back aperture of the objective.

4. The system of claim 3, wherein the one or more relay lenses comprises two relay lenses, and the optical system further comprises an optical beam dump placed between the two relay lenses such that the optical beam dump absorbs lower-order diffraction maxima in excitation light that has interacted with the first SLM.

5. The system of claim 1, wherein the optical system further comprises an optical beamsplitter, wherein the optical beamsplitter directs excitation light that has interacted with the first SLM to the sample and transmits the emission light from the sample to the second SLM.

6. The system of claim 1, wherein the optical system further comprises a half-wave plate, wherein the half-wave plate changes a polarization direction of the excitation light.

7. The system of claim 1, wherein the first SLM comprises at least one of a liquid crystal device (LCD) or a liquid crystal-on-silicon (LCOS) device.

8. The system of claim 1, wherein the second SLM comprises at least one of a digital micromirror device (DMD), a liquid crystal device (LCD), or a liquid crystal-on-silicon (LCOS) device.

9. The system of claim 1, wherein the optical system further comprises one or more tube lenses, wherein the one or more tube lenses image the pattern of pinholes to the imaging device.

10. The system of claim 9, wherein the one or more tube lenses comprises a pair of tube lenses, and the dispersive element is placed between the pair of tube lenses.

11. The system of claim 1, further comprising a controller operably coupled to the first SLM, the second SLM, the light source, and the imaging device, wherein the controller is configured to modulate pixels of the first and second SLMs, to operate the light source, and to operate the imaging device.

12. The system of claim 1, wherein:
the optical system is further configured to illuminate the sample sequentially in a series of excitation patterns that are shifted from one another,
the second SLM is configured to form a series of patterns of pinholes, wherein each pattern in the series of patterns of pinholes matches a corresponding excitation pattern in the series of excitation patterns, and
each image in the plurality of images corresponds to an excitation pattern in the series of excitation patterns.

13. The system of claim 1, wherein:
the excitation pattern comprises a plurality of excitation spots, and
each image of the plurality of images comprises a plurality of fluorescent emission spectra.

14. A method for obtaining a confocal image, comprising:
providing, from a light source, excitation light having one or more wavelengths;
collimating the excitation light from the light source;
applying, by a first spatial light modulator (SLM), a predetermined phase modulation pattern to the collimated excitation light;
using the phase-modulated collimated excitation light to form a two-dimensional excitation pattern to illuminate a sample, wherein the excitation pattern is formed at a focal plane within the sample;
collecting emission light from the focal plane within the sample;
directing the collected emission light to an imaging device via a second SLM, wherein the focal plane within the sample is conjugate to a plane of a pattern of pinholes formed by pixels of the second SLM;
spectrally dispersing the collected emission light with a pair of double Amici prisms before the collected emission light reaches the imaging device;
obtaining, using the imaging device, a plurality of images of the spectrally dispersed emission light; and
reconstructing the plurality of images to provide a hyperspectral confocal image dataset of the sample.

15. The method of claim 13, further comprising controlling a polarization of the excitation light using a half-wave plate.

16. The method of claim 13, further comprising
focusing, using an objective, the collimated excitation light that has interacted with the first SLM onto the focal plane within the sample; and
imaging the phase modulation pattern onto a back aperture of the objective using one or more relay lenses.

17. The method of claim 16, wherein the one or more relay lenses comprises two relay lenses, and the method further comprises absorbing, using an optical beam dump placed between the two relay lenses, lower-order diffraction maxima in excitation light that has interacted with the first SLM.

18. The method of claim 13, further comprising imaging the pattern of pinholes to the imaging device using one or more tube lenses.

19. The method of claim 18, further comprising
illuminating the sample sequentially in a series of excitation patterns that are shifted from one another; and
forming, with the second SLM, a series of patterns of pinholes, wherein each pattern in the series of patterns of pinholes matches a corresponding excitation pattern in the series of excitation patterns.

20. The method of claim 19, wherein each image in the plurality of images corresponds to an excitation pattern in the series of excitation patterns.

* * * * *